(12) United States Patent
Lim et al.

(10) Patent No.: US 11,234,863 B2
(45) Date of Patent: Feb. 1, 2022

(54) EYE DROP GUIDE DEVICE FOR INSTILLING EYE DROPS

(71) Applicants: SINGAPORE NATIONAL EYE CENTRE PTE LTD, Singapore (SG); NGEE ANN POLYTECHNIC, Singapore (SG)

(72) Inventors: Priscilla Shiow Huey Lim, Singapore (SG); Lam Wing Tan, Singapore (SG)

(73) Assignees: SINGAPORE NATIONAL EYE CENTRE PTE LTD, Singapore (SG); NGEE ANN POLYTECHNIC, Singapore (SG)

( * ) Notice: Subject to any disclaimer, the term of this patent is extended or adjusted under 35 U.S.C. 154(b) by 109 days.

(21) Appl. No.: 16/622,290

(22) PCT Filed: Jun. 11, 2018

(86) PCT No.: PCT/SG2018/050291
§ 371 (c)(1),
(2) Date: Dec. 13, 2019

(87) PCT Pub. No.: WO2018/231150
PCT Pub. Date: Dec. 20, 2018

(65) Prior Publication Data
US 2020/0206031 A1    Jul. 2, 2020

(30) Foreign Application Priority Data

Jun. 15, 2017  (SG) ............................. 10201704927S

(51) Int. Cl.
*A61F 9/00*    (2006.01)

(52) U.S. Cl.
CPC ...... *A61F 9/0026* (2013.01); *A61F 2210/009* (2013.01); *A61F 2210/0071* (2013.01)

(58) Field of Classification Search
CPC ............ A61F 9/0026; A61F 2210/0071; A61F 2210/009; A61F 9/0008; A61F 9/00;
(Continued)

(56) References Cited

U.S. PATENT DOCUMENTS 4,531,944 A * 7/1985 Bechtle ................. A61F 9/0026
604/302
5,154,711 A * 10/1992 Williams .............. A61F 9/0026
604/301

(Continued)

FOREIGN PATENT DOCUMENTS

CN      201743826 U    2/2011
WO   2006126971 A1   11/2006

*Primary Examiner* — Tatyana Zalukaeva
*Assistant Examiner* — Hans Kaliher
(74) *Attorney, Agent, or Firm* — Soroker Agmon Nordman PTE LTD

(57) ABSTRACT

An eye drop guide for instilling eye drops to an eye includes an eye cup housing and an eye drop dispenser holder. The eye cup housing includes an eye cup at a first end of the eye cup housing configured to be placed over an eye, a hole through the eye cup housing at a second end of the eye cup housing, and a magnet fixed to the eye cup housing at the second end. The eye drop dispenser holder may include a magnet fixed to the eye drop dispenser holder. The magnet in the eye cup housing and the magnet in the eye drop dispenser holder are configured to be attracted to one another so as to removably attach the eye cup housing to the eye drop dispenser holder.

19 Claims, 12 Drawing Sheets

(58) Field of Classification Search
CPC ..... A61F 2009/0043; A61F 2009/0052; B65D 1/08; B65D 47/18; B65D 47/185
See application file for complete search history.

(56) References Cited

U.S. PATENT DOCUMENTS

| | | | |
|---|---|---|---|
| 5,382,243 A | 1/1995 | Mulholland | |
| 2005/0029307 A1* | 2/2005 | Py | B65D 81/245 222/386 |
| 2008/0208148 A1* | 8/2008 | Soon | A61M 35/10 604/301 |
| 2010/0331765 A1 | 12/2010 | Sullivan et al. | |
| 2014/0371688 A1 | 12/2014 | Abbassi | |
| 2015/0223977 A1* | 8/2015 | Oberkircher | A61M 5/158 604/521 |
| 2020/0095055 A1* | 3/2020 | Cailloux | B05B 11/0027 |

\* cited by examiner

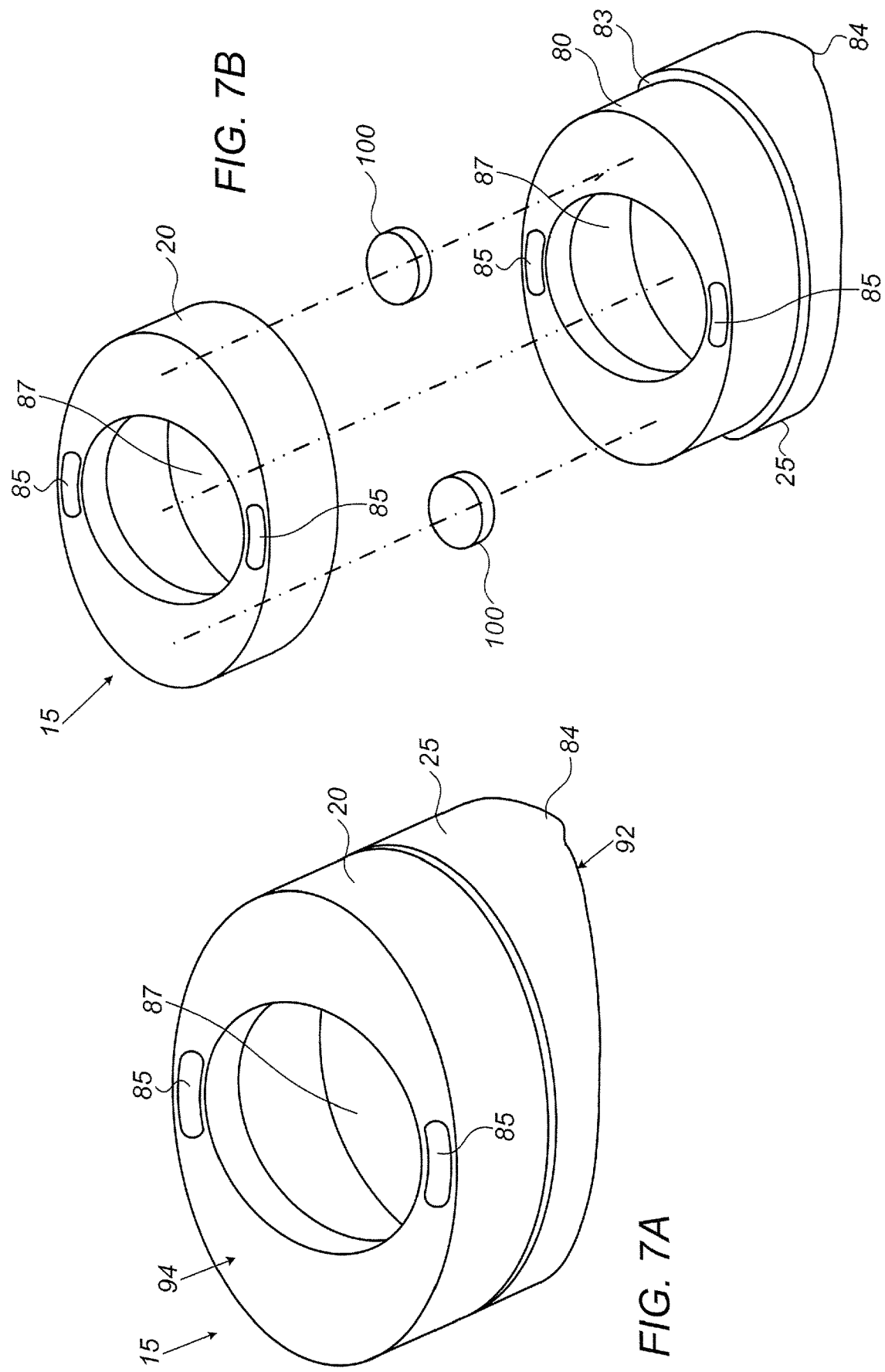

EYE DROP GUIDE DEVICE FOR INSTILLING EYE DROPS

FIELD OF THE INVENTION

The present invention relates to an eye drop dispensing guide. More specifically, the present invention relates to an eye drop guide device for instilling eye drops into an eye.

BACKGROUND OF THE INVENTION

Many eye complications, illnesses, and/or pathologies may be treated by the use of medications delivered to the eye, typically in the form of eye drops. However, the self-administration of eye drops by a patient may be problematic in the case where no care-giver may be present to assist. For example, the patient typically needs to open the eye drop dispenser, use his/her fingers to hold open the eye lids to expose the eyeball, to align the eye drop dispenser tip with the exposed eyeball, and to administer the proper eye drop dosage onto the exposed eyeball.

Typically, the patient may not see the tip of the eye drop dispenser as the cornea of eye may instinctively be either rolled downward or upward when the patient uses his fingers to open the eyelids. Thus, as the patient squeezes the dispenser, the eye drops may fall away from the exposed eyeball onto the eyelids and/or cheeks of the patient. In some cases, the patient may then try to apply more eye drops to compensate the loss of the eye drops resulting in applying more drops than the recommended dosage (e.g., over-dosage) as well as wasting the eye drop medication. In some cases, the patient may not apply enough of eye drops medication necessary to alleviate the eye illness or pathology. In some cases, the patient may be too elderly and not be able to self-administer the eye drop medication.

The scenarios become particularly critical in cases, for example, where high intra-ocular pressures such as from glaucoma require eye drop medications need to be regularly applied to reduce the pressure to normal levels to prevent blindness and/or in cases where eye drops medications are needed to restore vision after eye surgery. Patients may also have to apply multiple eye drop medications where each eye drop medication has a different eye drop dispenser shape and size.

Thus, it may be desirable to have an auto-aiming eye drop guide device which interchangeably accommodates multiple eye drop dispensers of different shapes and sizes so as to assist patients in accurately instilling eye drop medications.

SUMMARY OF THE INVENTION

There is thus provided, in accordance with some embodiments of the present invention, an eye drop guide for instilling eye drops to an eye. The eye drop guide includes an eye cup housing and an eye drop dispenser holder. The eye cup housing may include an eye cup at a first end of the eye cup housing configured to be placed over an eye, a hole through the eye cup housing at a second end of the eye cup housing, and a magnet fixed to the eye cup housing at the second end. The eye drop dispenser holder may include a magnet fixed to the eye drop dispenser holder. The magnet in the eye cup housing and the magnet in the eye drop dispenser holder are configured to be attracted to one another so as to removably attach the eye cup housing to the eye drop dispenser holder that positions a tip of an eye drop dispenser held by the eye drop dispenser holder to pass through the hole in the eye cup housing and into the eye cup for instilling eye drops into the eye.

Furthermore, the eye drop dispenser holder may include a steel plate fixed to the eye drop dispenser holder.

Furthermore, in accordance with some embodiments of the present invention, the eye cup is contoured with a curvature of an eye socket.

Furthermore, in accordance with some embodiments of the present invention, the magnet is fixed to the eye cup housing by placing the magnet in a respective socket formed in the eye cup housing, and wherein the magnet is fixed to the eye drop dispenser holder by placing the magnet in a respective socket formed in the eye drop dispenser holder.

Furthermore, in accordance with some embodiments of the present invention, the eye cup housing comprises one or more light holes.

Furthermore, in accordance with some embodiments of the present invention, the eye cup housing includes an eye cup housing base, and an eye cup housing case with a socket at the second end formed therein adjacent to the hole and configured to be placed over the eye cup housing base.

Furthermore, in accordance with some embodiments of the present invention, the eye cup and the eye cup housing base are formed from silicone.

Furthermore, in accordance with some embodiments of the present invention, the eye cup housing case is formed from a thermoplastic.

Furthermore, in accordance with some embodiments of the present invention, the eye cup housing case affixes the magnet in the socket at the second end when placed over the eye cup housing base.

Furthermore, in accordance with some embodiments of the present invention, the eye drop dispenser holder includes a guide wall configured to support to the second end of the eye cup housing when attached to the eye drop dispenser holder.

Furthermore, in accordance with some embodiments of the present invention, a socket is formed in a tab attached to the eye drop dispenser holder for holding the magnet in the eye drop dispenser holder.

Furthermore, in accordance with some embodiments of the present invention, the eye drop dispenser holder includes an eye drop dispenser holder body and an eye drop dispenser holder case.

Furthermore, in accordance with some embodiments of the present invention, the eye drop dispenser holder body and the eye drop dispenser holder case are formed from a thermoplastic.

Furthermore, in accordance with some embodiments of the present invention, the eye drop dispenser holder is configured to hold an eye drop bottle using a flexible membrane attached to the eye drop dispenser holder.

Furthermore, in accordance with some embodiments of the present invention, the flexible membrane includes an aperture with flaps configured to hold a neck of the eye drop bottle.

Furthermore, in accordance with some embodiments of the present invention, the eye drop dispenser holder is configured to hold a minim in a minim hole formed in the eye drop dispenser holder.

Furthermore, in accordance with some embodiments of the present invention, the eye drop dispenser holder includes a landing pad.

Furthermore, in accordance with some embodiments of the present invention, the eye drop dispenser holder includes restrictors.

Furthermore, in accordance with some embodiments of the present invention, the eye drop dispenser holder includes finger squeeze tabs.

Furthermore, in accordance with some embodiments of the present invention, the eye drop dispenser holder includes compression trusses.

Furthermore, in accordance with some embodiments of the present invention, the eye drop dispenser holder is formed from nylon.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

FIG. 7A schematically illustrates a top view of a fully assembled eye cup housing, in accordance with some embodiments of the present invention;

FIG. 7B schematically illustrates an exploded view of an eye cup housing, in accordance with some embodiments of the present invention;

DETAILED DESCRIPTION OF THE INVENTION

Figure 1A:
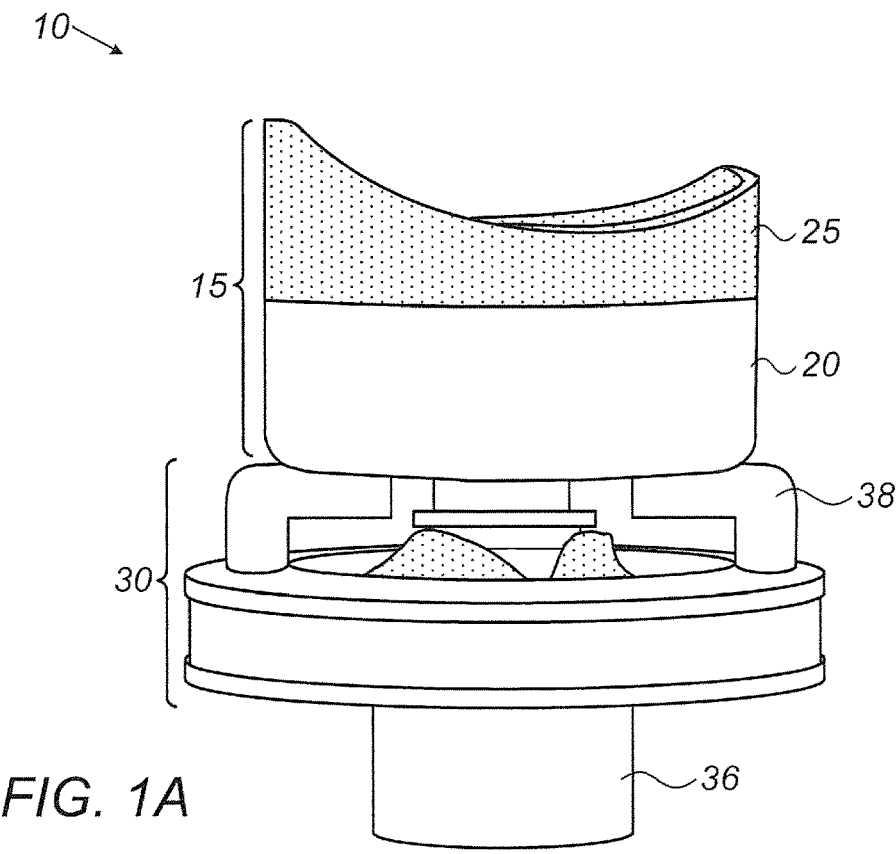
FIG. 1A schematically illustrates a side view of a first embodiment of an eye drop guide device, in accordance with some embodiments of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

Some embodiments of the present invention presented herein describe an eye drop guide device for assisting in instilling eye drops to an eye. Although the eye drop guide device taught herein may assist a user to self-administer eye drops to the user's eye, the eye drop guide may also be used, for example, by a health care professional to administer eye drops to a patient.

The eye drop guide device described herein may include an eye cup housing that is removably attached to an eye drop dispenser holder. Magnets may be located in sockets formed in both the eye cup housing and the eye drop dispenser housing are configured to be magnetically attracted to one another when a first set of magnets in the eye cup housing and a second set of magnets in the eye drop dispenser housing are substantially close and/or substantially opposite to one another. These magnets cause the eye cup housing to be firmly attached to the eye drop dispenser housing. "Removably attached" in the context of the patent application may be construed that the user can easily remove or pull apart the eye drop dispenser housing from the eye cup housing that are magnetically attached to one another.

In other embodiments of the present invention, one of the housings (e.g., the eye cup housing or the eye drop dispenser housing) may include a metal which is attracted to a magnet in the other housing. In this manner, only one of the housings may include a magnet. Thus, the term "magnet" in the context of this patent application may include a permanent magnet, and/or metal attracted to a permanent magnet (e.g., ferromagnetic materials such as iron, nickel and/or cobalt. Any suitable magnetic material may be used for removably attaching the eye drop dispenser housing to the eye cup housing in the context of the embodiments of the present invention described herein.

The eye drop dispenser housing may be configured to hold eye drop dispensers of different types, shapes, sizes, and/or form factors. The eye drop dispenser housing may support an eye drop bottle and/or a minim, for example. A user of the eye drop guide device may need to take varying dosages of more than one medication. For example, a first eye drop dispenser may be easily removed from the eye drop dispenser holder. A second eye drop dispenser may be subsequently installed and the eye cup holder may be removably attached to the eye drop dispenser holder ready for use.

The user may install the eye drop dispenser in the eye drop dispenser holder with the lid on which maintains sterility of the medication, and particularly the tip of the eye drop dispenser contacting the eye. The user may then open the eye drop dispenser exposing the tip of the eye drop dispenser and removably attach the eye cup holder. Moreover, the tip of the eye drop dispenser may be placed in the eye drop guide device such that when the eye drop guide device is placed over the eye, the tip of the bottle may be located substantially over the center of the eyeball (e.g. the cornea). The distance of the tip to the eyeball may also be configured to prevent the tip from touching the eyeball, particularly the cornea, so as to prevent injury.

FIG. 1A schematically illustrates a side view of a first embodiment of an eye drop guide device 10, in accordance with some embodiments of the present invention.

Figure 1B:
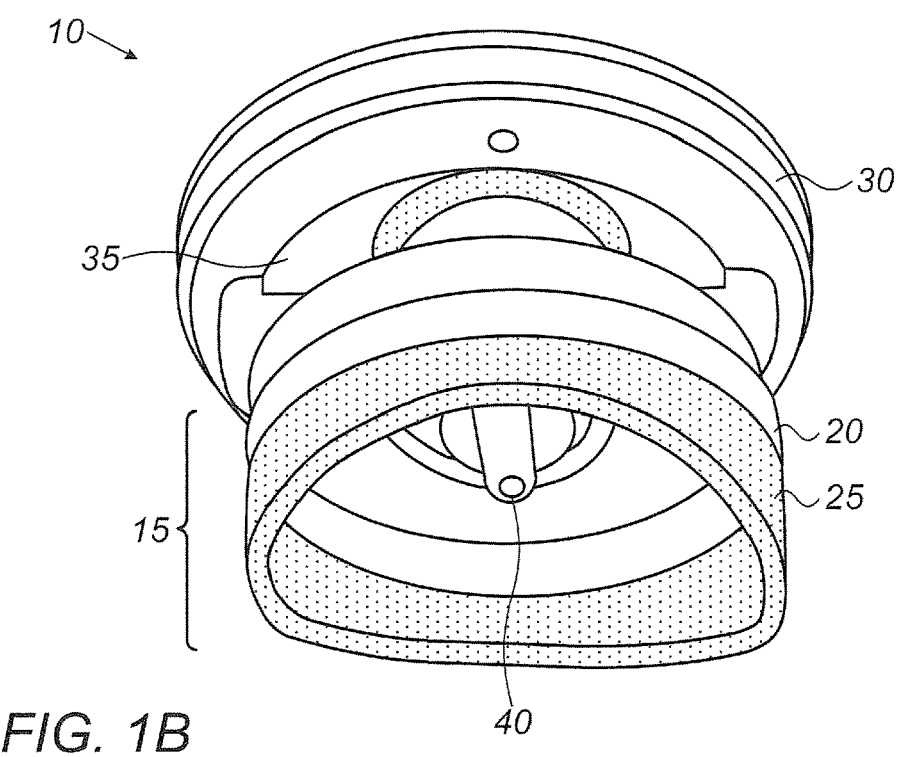
FIG. 1B schematically illustrates a perspective view of a first embodiment of an eye drop guide device, in accordance with some embodiments of the present invention.

FIG. 1B schematically illustrates a perspective view of a first embodiment of eye drop guide device 10, in accordance with some embodiments of the present invention.

In some embodiments of the present invention, eye drop guide device 10 may include an eye cup housing 15 and an eye drop dispenser holder 30. Eye drop dispenser 36 may include an eye drop bottle as shown in FIGS. 1A-1B such as a squeezable eye drop bottle where the user squeezes the bottle typically with the user's fingers to push the eye drops out from eye drop bottle 36 through a tip 40. For the embodiment shown in FIGS. 1A-1B, an eye drop dispenser 36 may be held in eye drop dispenser holder 30 with a flexible membrane 35 attached to eye drop dispenser holder 30. Eye cup housing 15 may include an eye cup 25 and an eye cup housing case 20.

In some embodiments of the present invention, tabs 38 attached to eye drop dispenser holder 30 may include a first set of magnets (not shown) assembled therein. Similarly, eye cup housing 15 may also include a second set of magnets where the first and second set of magnets have opposite polarities and are magnetically attracted to one another. This results in the tabs 38 snapping onto eye cup housing case 20 as shown FIG. 1A and being removably attached thereon.

Figure 1C:
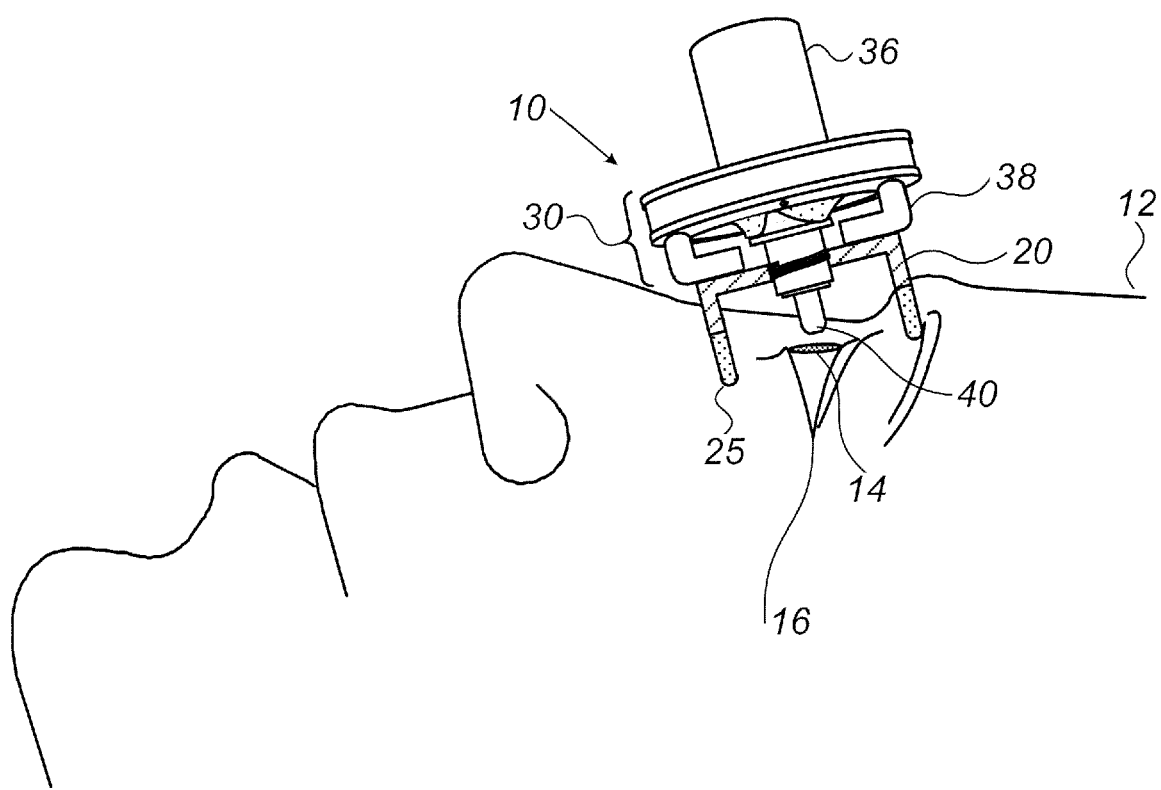
FIG. 1C schematically illustrates a user of a first embodiment of an eye drop guide device self-administering eye drops, in accordance with some embodiments of the present invention.

FIG. 1C schematically illustrates a user 12 of a first embodiment of eye drop guide device 10 self-administering eye drops, in accordance with some embodiments of the present invention. Eye cup 25 is placed over the user's eye socket. Eye cup housing 15 and an eye drop dispenser holder 30 are configured such that tip 40 of the eye drop bottle 36 is located substantially in the center of the eye cup (e.g., near to the center of a cornea 14). Moreover, eye drop dispenser holder 30 is configure to fix the distance of tip 40 to the edge of eye cup 25 is fixed in so as to prevent tip 40 from touching an eye 16 (e.g., cornea 14) during the application of the eye drops, thus preventing eye injury. User 12 can use his/her fingers to squeeze on eye drop dispenser 36 so as to dispense the eye drop through tip 40 to eye 16.

Figure 2A:
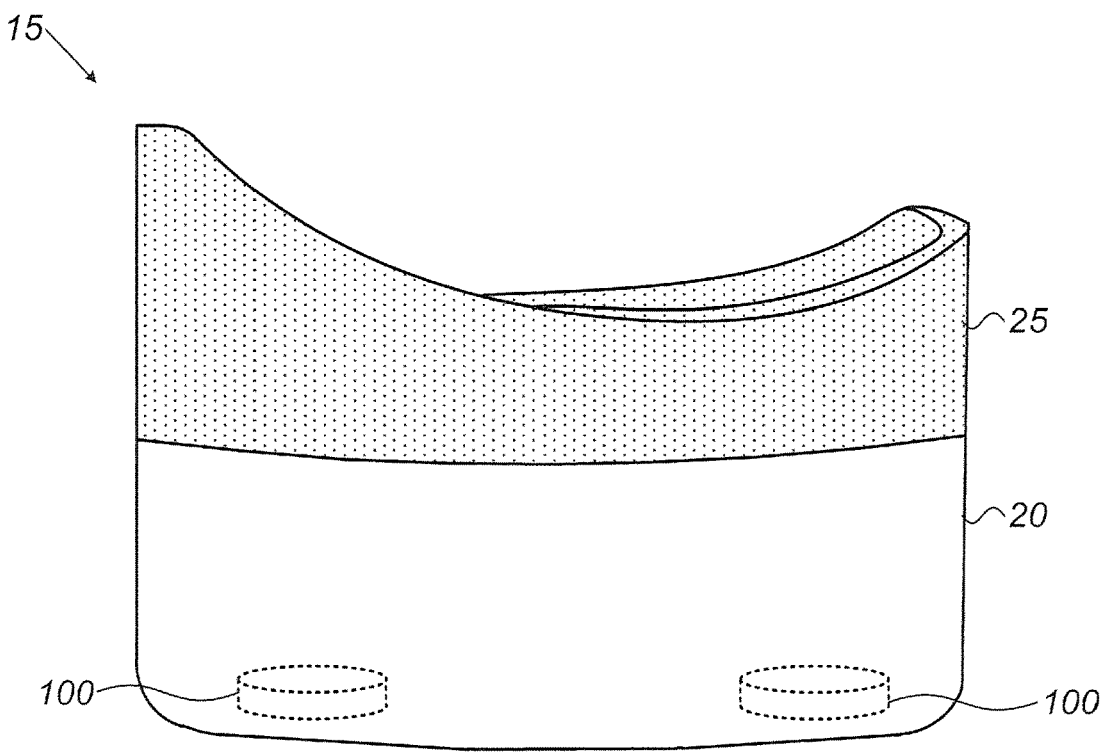
FIG. 2A schematically illustrates a side view of an eye cup housing, in accordance with some embodiments of the present invention.

FIG. 2A schematically illustrates a side view of eye cup housing 15, in accordance with some embodiments of the present invention. Eye cup housing 15 may include eye cup 25 and an eye cup housing case 20. Eye cup 25 may be contoured to the shape of an eye socket, and contoured outwards to hold the eyelids open. Eye cup housing 15 may be configured to be placed over an eye. Eye cup 25 may be simply rotated for placement over the right eye or the left eye of user 12 as needed. Two magnets 100 may be placed within sockets formed within eye cup housing 15 and positioned substantially opposite to one another.

Figure 2B:
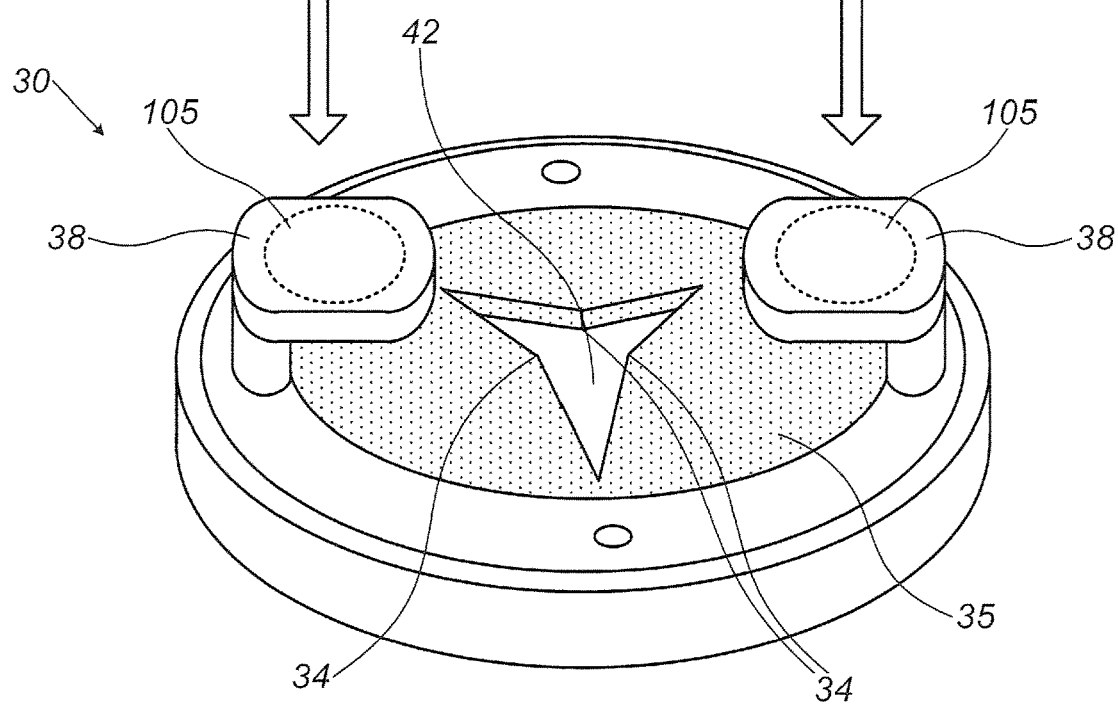
FIG. 2B schematically illustrates a top view of a first embodiment of an eye drop dispenser holder, in accordance with some embodiments of the present invention.

FIG. 2B schematically illustrates a top view of a first embodiment of an eye drop dispenser holder 30, in accordance with some embodiments of the present invention. Eye drop dispenser holder 30 may include tabs 38, flexible membrane 35, and an aperture 42 in flexible membrane 35. A user may push eye drop bottle 36 through aperture 42 and flaps 34 in flexible membrane 35 may be used to elastically apply pressure to the body of eye drop bottle 36 and hold eye drop bottle 36 in place. Two magnets 105 may be placed in sockets formed with tabs 38 attached to eye drop dispenser holder 30 positioned substantially opposite to one another. In some other embodiments, two pieces of steel plates or other material which magnets attract too may replace two magnets 105 and be placed in sockets formed with tabs 38. In some other embodiments, a single piece of magnet 105 or a single piece of steel plate can be used when those are sufficient to attract the eye cup housing to the eye drop dispenser holder so as to be removably attached. As shown in FIG. 2A, the two arrows indicate that the magnets 100 are attached to magnets 105 in assembling eye drop guide device 10.

Figure 3A:
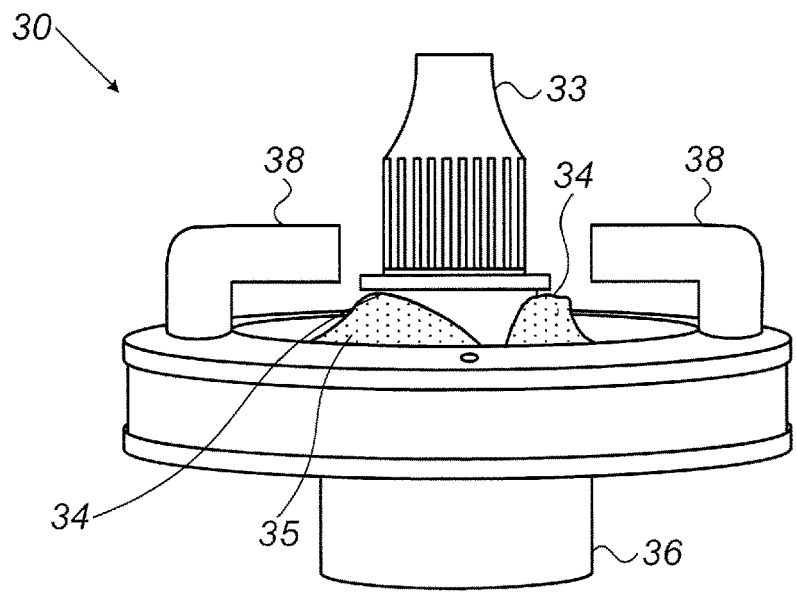
FIG. 3A schematically illustrates a top view of a first embodiment of an eye drop dispenser holder with a sealed eye drop bottle, in accordance with some embodiments of the present invention.

FIG. 3A schematically illustrates a top view of a first embodiment of an eye drop dispenser holder with eye drop bottle 36 that is sealed, in accordance with some embodiments of the present invention. Having eye drop bottle 36 sealed with a cap 33 maintains sterility of the eye drop medication before instilling the eye drops to the eyes. Once eye drop bottle 36 is placed through aperture 42 in flexible membrane 35, cap 33 may be removed.

Figure 3B:
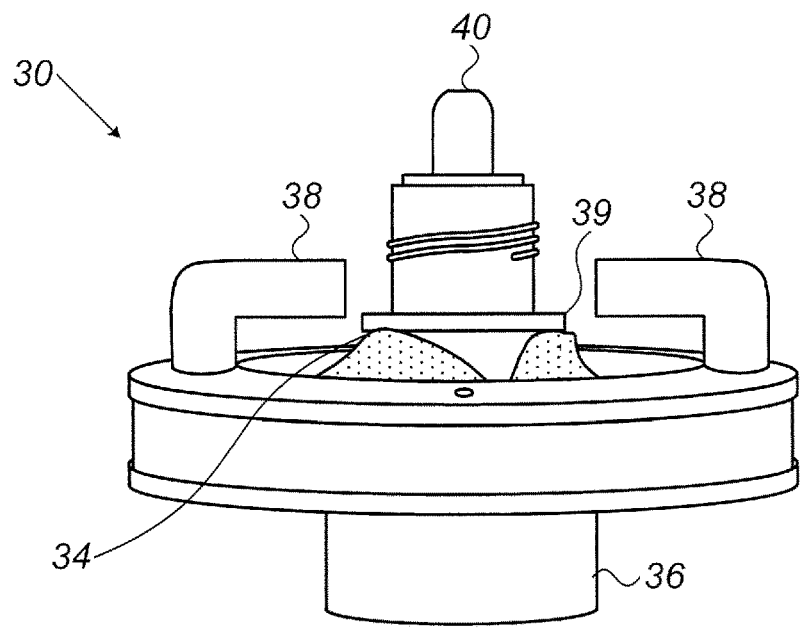
FIG. 3B schematically illustrates a side view of a first embodiment of an eye drop dispenser holder with an open eye drop bottle, in accordance with some embodiments of the present invention.

FIG. 3B schematically illustrates a side view of a first embodiment of eye drop dispenser holder 30 with eye drop bottle 36 that is opened, in accordance with some embodiments of the present invention. The side view of FIG. 3B further illustrates how eye drop dispenser holder 30 may be configured to hold eye drop bottle 36. In this embodiment, flaps 34 in aperture 42 of flexible membrane 35 may be used to catch or grip a neck 39 of eye drop bottle 36 so as to hold eye drop bottle 36 in place. Furthermore, flaps 34 may fix the position of tip 40 of eye drop bottle 36 when seated in aperture 42 in flexible membrane 35 before snapping eye cap housing 15 into place. In this manner, tip 40 may not touch the eyeball when applying the eye drops.

Figure 4A:
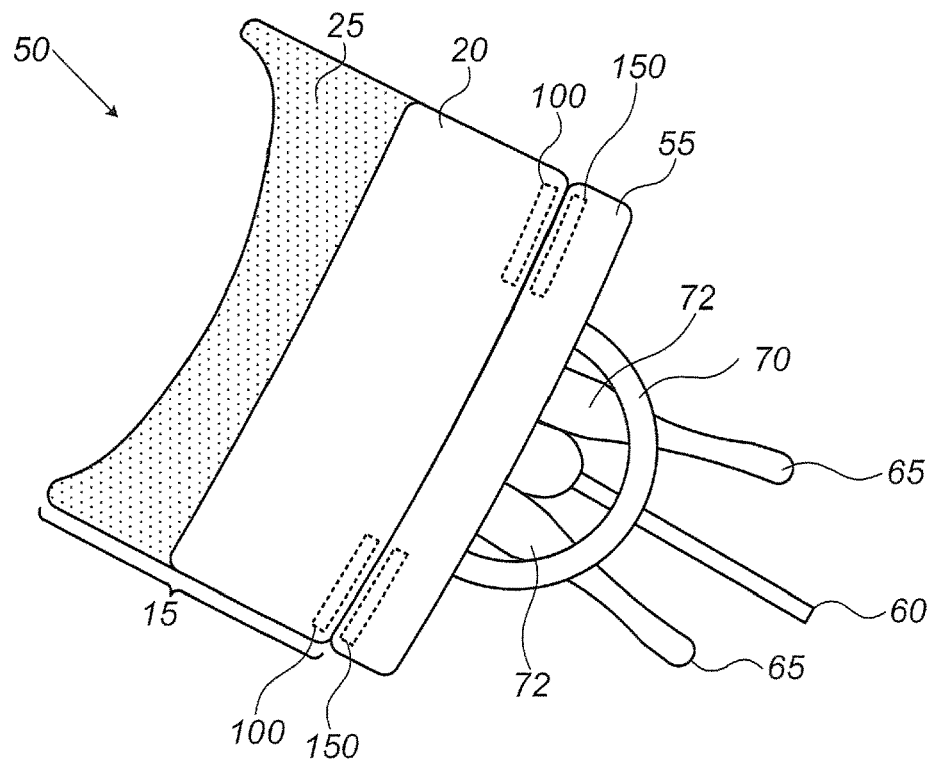
FIG. 4A schematically illustrates a side view of a second embodiment of an eye drop guide device, in accordance with some embodiments of the present invention.

FIG. 4A schematically illustrates a side view of a second embodiment of an eye drop guide device 50, in accordance with some embodiments of the present invention. Eye drop guide device 50 may include eye cup housing 15 and a second embodiment of an eye drop dispenser holder 55 for a minim 60 (e.g., eye drop dispenser). The term minim in the context of the present patent application refers to a plastic eye drop vial container, typically for a single use and/or single dosage. Two minim pressure tabs 72 may be used to apply pressure on the body of minim 60 when finger squeeze tabs 65 are squeezed together by the user. A restrictor 70 shown in FIG. 4A restricts the movement of minim 60 and holds the minim in place in eye drop dispenser holder 55.

FIG. 4A also schematically illustrates the relative positions in magnets 100 within eye cup housing 15 and magnets 150 within eye drop dispenser holder 55 in which the position and proximity of magnets 100 to magnets 150 causes the eye cup housing 15 to be removably attached to eye drop dispenser holder 55.

Figure 4B:
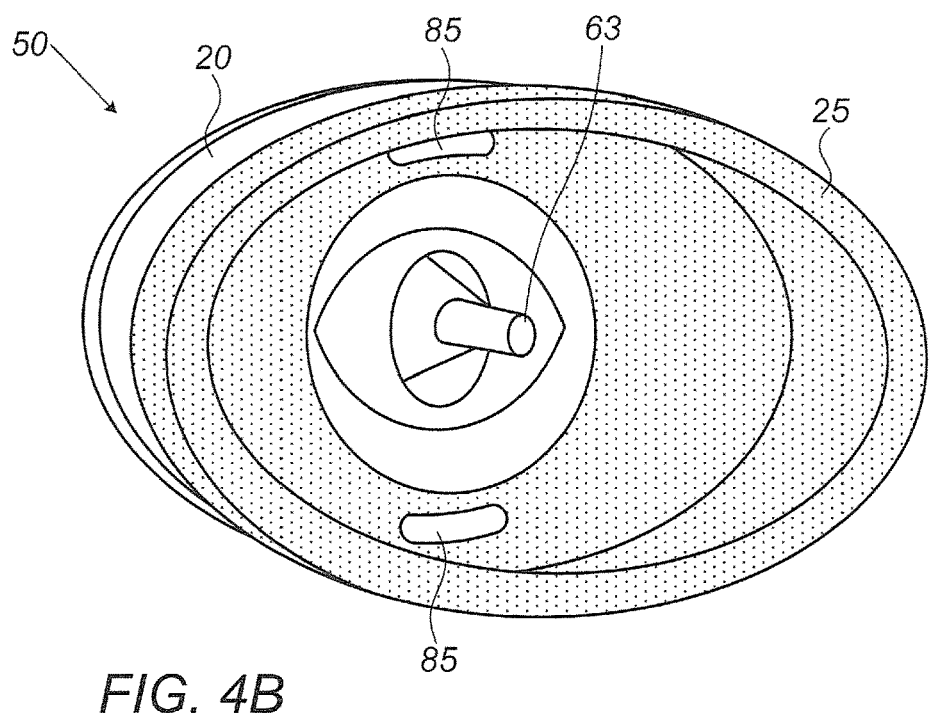
FIG. 4B schematically illustrates a top view of a second embodiment of an eye drop guide device, in accordance with some embodiments of the present invention.

FIG. 4B schematically illustrates a top view of a second embodiment of an eye drop guide device 50, in accordance with some embodiments of the present invention. A tip 63 of minim 60 passes into eye cup 25 placed over eye 16 of the user for instilling eye drops from minim 60 into eye 16. Once eye cup 25 of eye drop guide device 50 is placed over the user's eye, the user may apply pressure to squeeze tabs 65 so as to push out eye drops from minim 60 through tip 63 and into the user's eye. Note that although FIG. 1C schematically illustrates user 12 using eye drop guide device 10, device 10 in FIG. 1C may be interchanged with eye drop device 50 for minims 60.

Figure 5A:
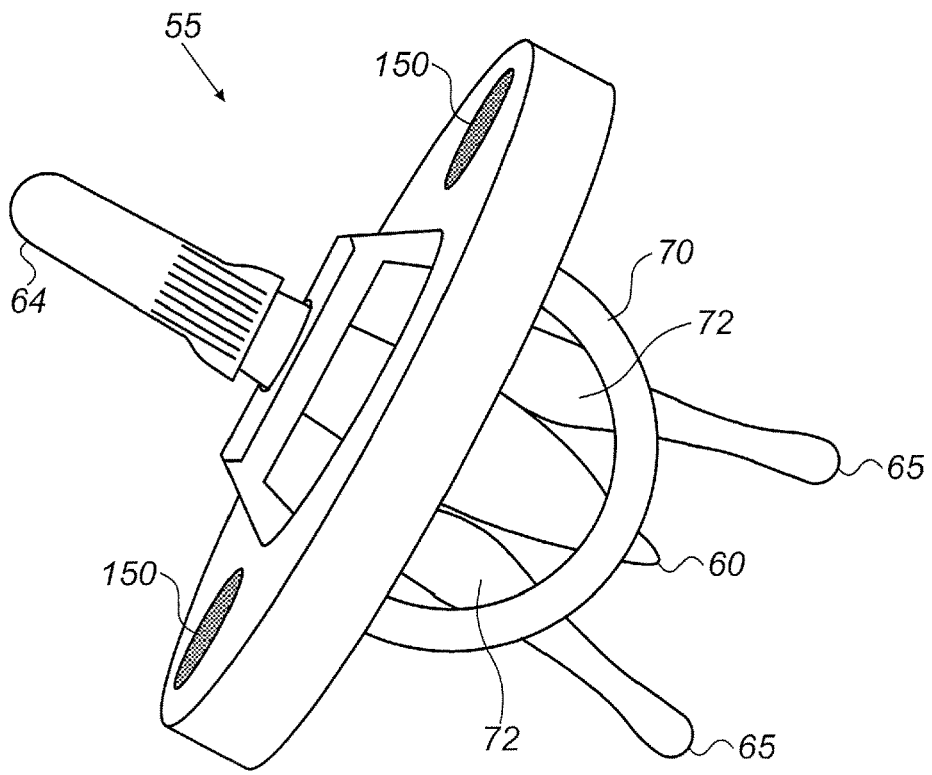
FIG. 5A schematically illustrates a side view of a second embodiment of an eye drop dispenser holder with a sealed minim, in accordance with some embodiments of the present invention.

FIG. 5A schematically illustrates a side view of a second embodiment of eye drop dispenser holder 55 with minim 60 sealed with a cap 64, in accordance with some embodiments of the present invention. Having minim 60 sealed with a cap 64 maintains sterility of the eye drop medication before instilling the eye drops to the eyes.

Figure 5B:
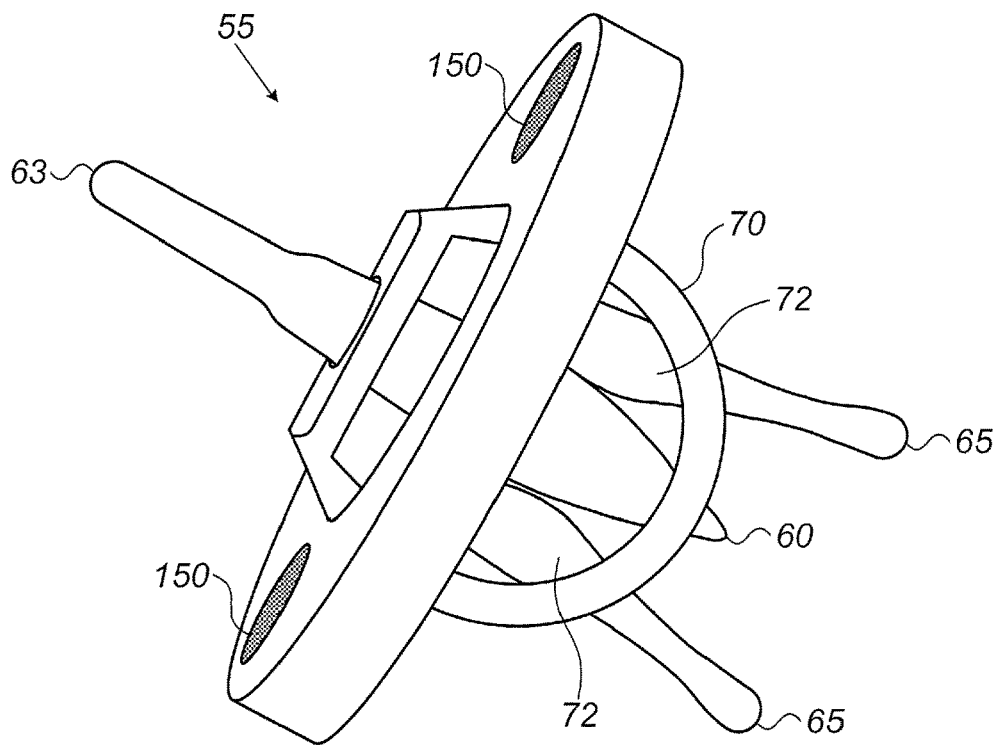
FIG. 5B schematically illustrates a side view of a second embodiment of an eye drop dispenser holder with an open minim, in accordance with some embodiments of the present invention.

FIG. 5B schematically illustrates a side view of a second embodiment of eye drop dispenser holder 55 with minim 60 open with tip 63, in accordance with some embodiments of the present invention. Once minim 60 is placed in eye drop dispenser holder 55, cap 64 may be removed to expose tip 63.

Figure 6B:
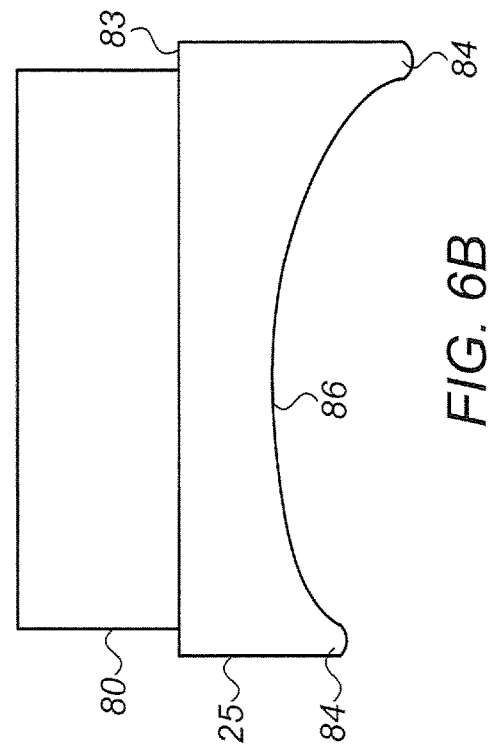
FIG. 6B schematically illustrates a side view of an eye cup housing base and an eye cup, in accordance with some embodiments of the present invention.
Figure 6A:
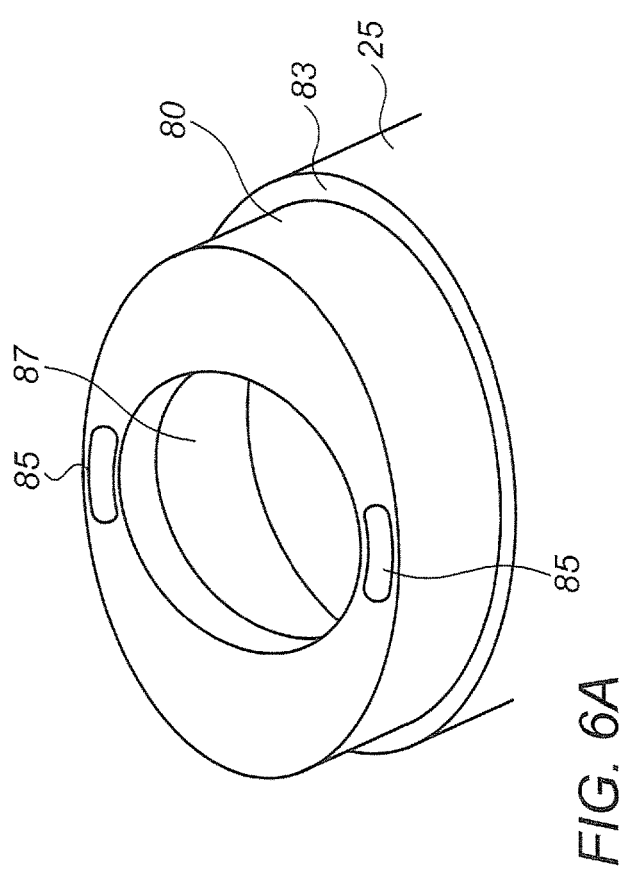
FIG. 6A schematically illustrates a top view of an eye cup housing base and an eye cup, in accordance with some embodiments of the present invention.

FIG. 6A schematically illustrates a top view of an eye cup housing base 80 and eye cup 25, in accordance with some embodiments of the present invention.

FIG. 6B schematically illustrates a side view of eye cup housing base 80 and eye cup 25, in accordance with some embodiments of the present invention.

In some embodiments of the present invention, eye cup housing base 80 may include a hole 87 for eye drop dispenser tips 40 and 63 to pass through and into eye cup 25. Eye cup housing base 80 may include light holes 85 formed thereon. Light holes 85 allow light to pass into eye cup 25. User 12 may focus on the illuminated light holes when the eye cup is positioned over the user's eye which reduces the tendency to blink when instilling the eye drops.

In some embodiments of the present invention, eye cup 25 may include a contour 86 shaped to the eye socket for provide a comfortable and stable fit. For example, contour 86 of eye cup 25 includes a protrusion 84 on one side of eye cup 25. Protrusion 84 may also indicate to the user that the side of eye cup 25 with protrusion 84 may be placed on the side of the eye opposite the nose. Eye cup 25 may also be rotated so as to be used interchangeably with each eye.

In some embodiments of the present invention, eye cup housing base 80 and eye cup 25 may be formed from a soft and compressive materials such as silicone, for example. The rubbery nature of the silicone contacting the skin causes skin friction. Skin friction may provide comfort to user 12 and may reduce the tendency to blink. Eye cup housing base 80 includes a rim 83 as a stopper for supporting eye cup housing case 20 when slid over and positioned onto eye cup housing base 80 so as to form eye cup housing 15.

Figure 6C:
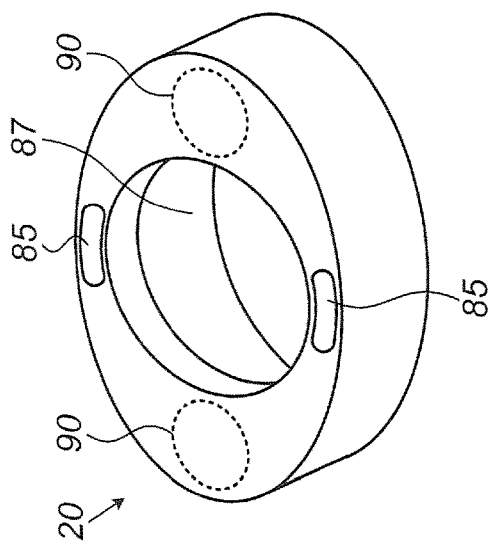
FIG. 6C schematically illustrates a top view of an eye cup housing case, in accordance with some embodiments of the present invention.

FIG. 6C schematically illustrates a top view of eye cup housing case 20, in accordance with some embodiments of the present invention. Eye cup housing case 20 may be formed from a thermoplastic material, which is hard, strong, and light weight, and may provide support and stability to the eye cup housing base 80 formed from silicone. Two sockets 90 are formed in eye cup housing case 20 (on the bottom side) for holding the magnets used in docking eye cup housing 15 to eye drop dispenser holders 30 and 55. Eye cup housing case 20 may also include light holes 85 as described previously.

FIG. 7A schematically illustrates a top view of fully assembled, eye cup housing 15, in accordance with some embodiments of the present invention.

FIG. 7B schematically illustrates an exploded view of eye cup housing 15, in accordance with some embodiments of the present invention.

Eye cup housing 15 includes eye cup 25 at a first end 92 of eye cup housing 15, and hole 87 and sockets 90 with magnets 100 at a second end 94 of eye cup housing 15, the magnets held in place by eye cup housing case 20. For the embodiment of FIG. 7A, second end 94 of eye cup housing 15 may have an oval shape or contour, although any suitable shape or contour may be used. In the embodiment shown in FIGS. 7A and 7B, two magnets 100 may be used in eye cup housing 15 so as to better align eye cup housing 15 with any suitable eye drop dispenser holder, such as eye drop dispenser holders 30 and 55. Having magnets 100 to removably attach eye cup housing 15 to magnets 105 and/or 150 in respective eye drop dispenser holders 30 and/or 55 also reduces wear and tear on the components of the eye drop guide devices, which increases the life span of the eye drop guide devices.

Figure 8A:
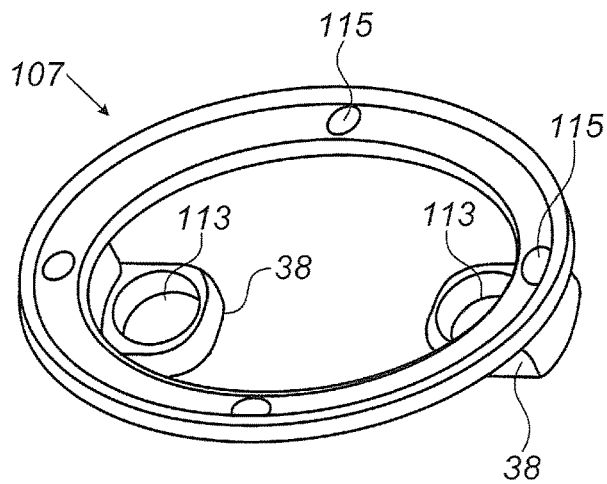
FIG. 8A schematically illustrates a top view of an eye drop dispenser holder body, in accordance with some embodiments of the present invention.

FIG. 8A schematically illustrates a top view of an eye drop dispenser holder body 107, in accordance with some embodiments of the present invention. Eye drop dispenser holder body 107 may include sockets 113 formed in tabs 38 for holding magnets, and holes 115 for receiving locking pins 125 (see FIG. 8D). Eye drop dispenser holder body 107 is the primary support for the assembly of eye drop dispenser holder 30. Eye drop dispenser holder body 107 may be formed from a thermoplastic material, which is hard, strong, and light weight.

Figure 8B:
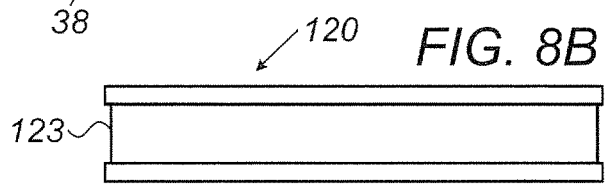
FIG. 8B schematically illustrates a side view of an eye drop dispenser holder case, in accordance with some embodiments of the present invention.

FIG. 8B schematically illustrates a side view of an eye drop dispenser holder case 120, in accordance with some embodiments of the present invention.

Figure 8C:
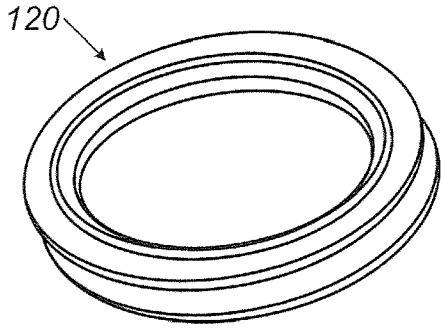
FIG. 8C schematically illustrates a top view of an eye drop dispenser holder case, in accordance with some embodiments of the present invention.

FIG. 8C schematically illustrates a top view of eye drop dispenser holder case 120, in accordance with some embodiments of the present invention.

Figure 8D:
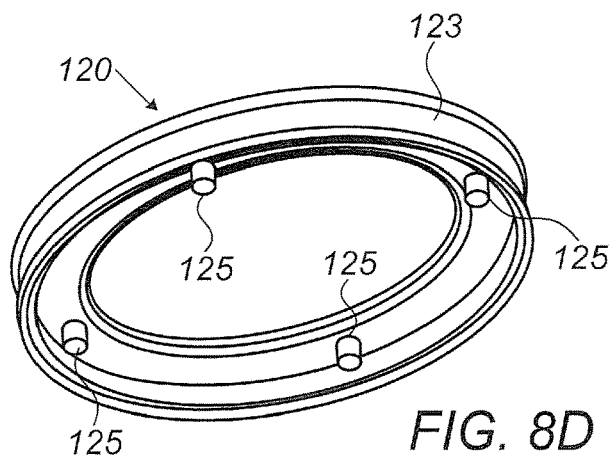
FIG. 8D schematically illustrates a bottom view of an eye drop dispenser holder case, in accordance with some embodiments of the present invention.

FIG. 8D schematically illustrates a bottom view of an eye drop dispenser holder case 120, in accordance with some embodiments of the present invention.

Figure 8E:
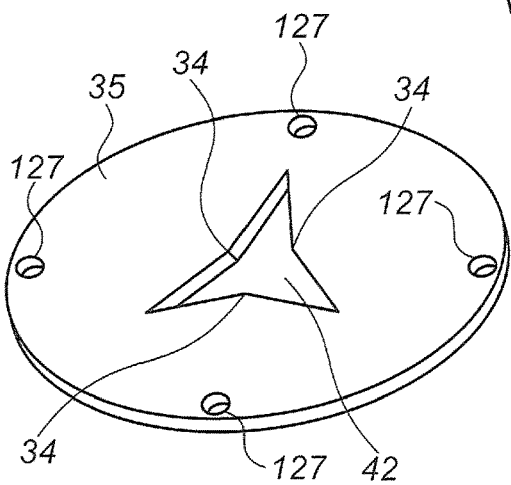
FIG. 8E schematically illustrates a top view of a flexible membrane, in accordance with some embodiments of the present invention.
Figure 8F:
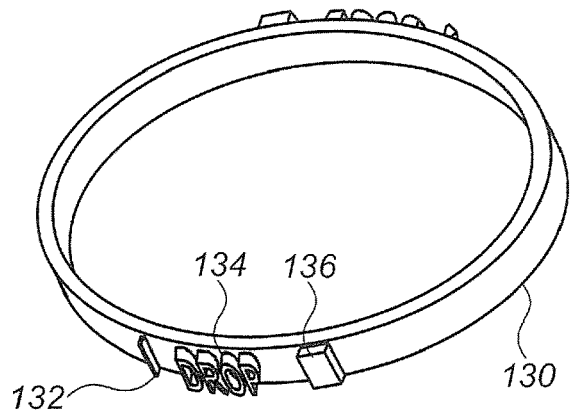
FIG. 8F schematically illustrates a top view of a prescription band, in accordance with some embodiments of the present invention.

Eye drop dispenser holder case 120 includes an indentation 123 for the placement or strapping of a prescription band 130 around eye drop dispenser holder case 120 (see FIG. 8F). Eye drop dispenser holder case 120 may be formed from a thermoplastic material, which is hard, strong, and light-weight. As shown in FIG. 8D, eye drop dispenser holder case 120 may include locking pins 125 which may be used to hold flexible membrane 35 and connect eye drop dispenser holder case 120 to eye drop dispenser holder body 107.

FIG. 8E schematically illustrates a top view of flexible membrane 35, in accordance with some embodiments of the present invention. Flexible membrane 35 includes aperture 42, which has a near triangular shape, for example, with flaps 34, and locking pin hole 127 as shown in FIG. 8E. Locking pin holes 127 allow locking pins 125 to catch and hold flexible membrane 35 in eye drop dispenser holder 30. Flexible membrane 35 may be formed from flexible silicone, for example. Aperture 42 may be formed by molding the silicone and/or cutting the silicone to the shape shown in FIG. 8E. The near-triangular shape of aperture 42 is not by way of limitation of the embodiments of the present invention, any suitably shaped aperture may be used to hold eye drop dispenser 36 in the manner described herein.

In some embodiments of the present invention, aperture 42 may be placed in the center of flexible membrane 35 such that that the center of the aperture will line up with tip 40 of eye drop bottle 36 when eye drop (bottle) dispenser 36 is pushed through the aperture. Flaps 34 help to catch neck 39 of eye drop (bottle) dispenser 36. The size of aperture 42 is large enough to support most shapes and sizes of eye drop (bottle) dispenser 36 when pushed through aperture 42. Yet, aperture 42 is small enough that the flaps 34 and/or walls of aperture 42 in flexible membrane 35 elastically squeezes around the body of eye drop (bottle) dispenser 36 so as to hold eye drop (bottle) dispenser 36 firmly in place in flexible membrane 35.

In some embodiments of the present invention, the aperture geometry and pliancy of flexible membrane 35 may also help position tip 40 passing through hole 87 to be substantially in the center of eye cup 25 when eye cup housing 15 is removably attached to eye drop dispenser holder 30 as shown in FIG. 1C. This self-centering of tip 40 in the design of the eye drop guide devices helps to ensure that when user 12 squeezes eye drops from eye drop (bottle) dispenser 36, the eye drops will be auto-aimed landing substantially in the center of eye 16 (e.g., on cornea 14).

FIG. 8F schematically illustrates a top view of prescription band 130, in accordance with some embodiments of the present invention. Prescription band 130 may be configured to be placed and/or wrapped around indentation 123. Prescription band 130 may be formed from a latex material, which is strong, flexible and light-weight. Prescription band 130 may include visual and/or tactile indicia to assist user 12 to identifying the dosage (e.g., number of eye drops to be instilled in eye 16) and/or identification of the eye or eyes for the eye drops to be instilled (e.g., in the right eye, left eye, or both eyes) and/or the type of medication in accordance with specific eye drop bottle to be used. For example, the indicia may include a visual indication 132 of the quantity of eye drops to be instilled, a tactile indication 134 of the number of eye drops to be instilled (e.g., for the visually impaired), and a colored prescription band 136. Colored prescription band may include different colors to indicate different eye drop quantities to be instilled, such as for example, 1 drop—red, 2 drops—blue, 3 drops—yellow. For color-blind individuals, the different color indicia may include: 1 drop—red-purple, 2 drops—blue-green, 3 drops—yellow-orange.

Figure 9A:
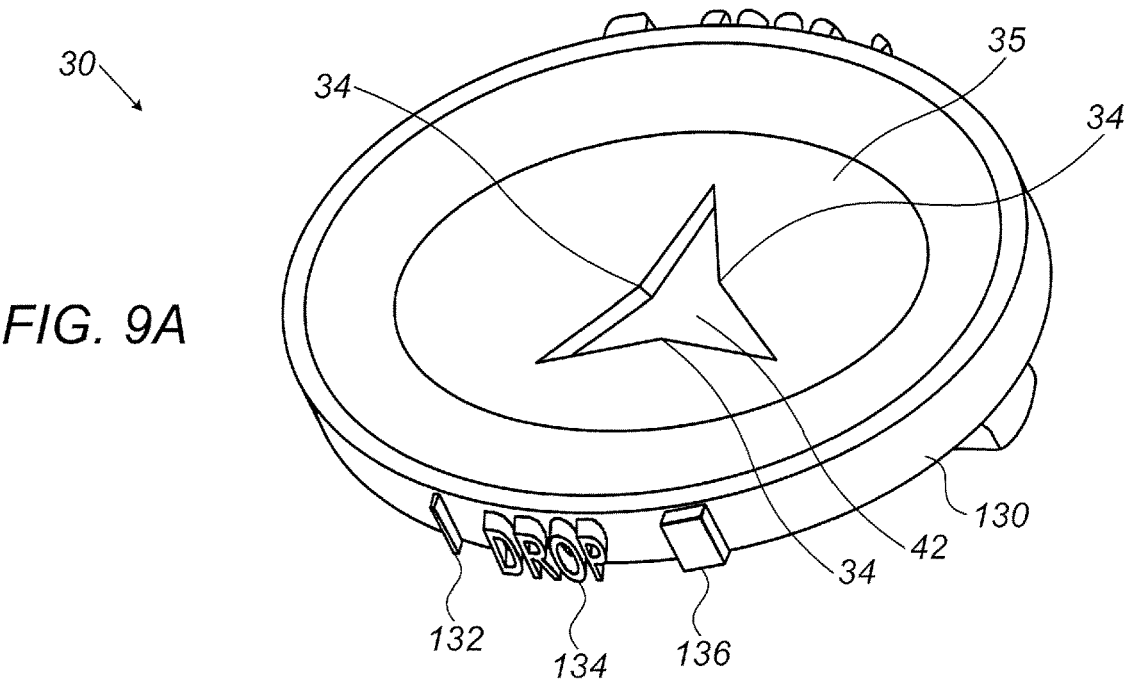
FIG. 9A schematically illustrates a top view of first embodiment of a fully assembled eye drop dispenser holder, in accordance with some embodiments of the present invention.

FIG. 9A schematically illustrates a top view of first embodiment of a fully assembled, eye drop dispenser holder 30, in accordance with some embodiments of the present invention.

Figure 9B:
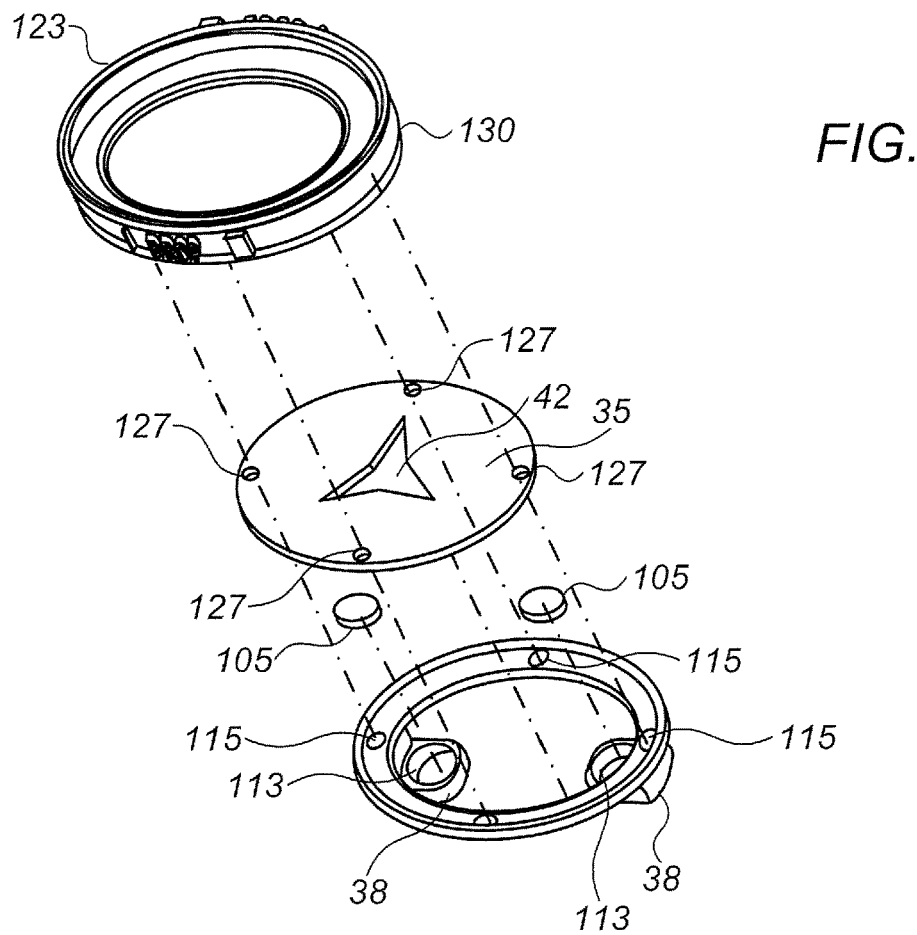
FIG. 9B schematically illustrates an exploded view of a first embodiment of an eye drop dispenser holder, in accordance with some embodiments of the present invention.

FIG. 9B schematically illustrates an exploded view of a first embodiment of an eye drop dispenser holder 30, in accordance with some embodiments of the present invention.

In some embodiment of the present invention, eye drop dispenser holder 30 may be assembled in the following exemplary manner for eye drop guide device 10. First, two magnets 105 may be installed in sockets 113 in eye drop dispenser holder body 107. Flexible membrane 35 may be placed on eye drop dispenser holder body 107 with locking pins holes 127 on flexible membrane 35 aligned with locking pin holes 115 on eye drop dispenser holder body 107. Eye drop dispenser holder case 120 may then be connected to the assembly with locking pins 125 passing through locking pin holes 115 and 127. Finally, prescription band 130 may be wrapped around indentation 123. Fully assembled, eye drop dispenser holder 30 may be then removably attached to eye cup housing 15 to form eye drop guide device 10.

Figure 10A:
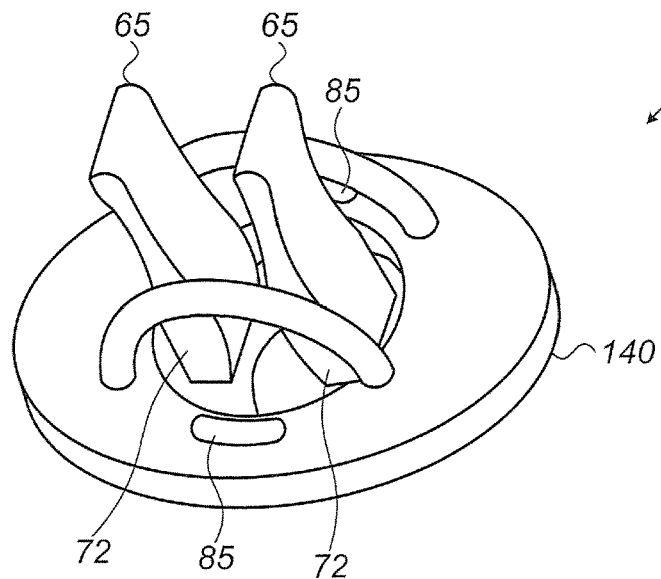
FIG. 10A schematically illustrates a top view of a second embodiment of an eye drop dispenser holder, in accordance with some embodiments of the present invention.

FIG. 10A schematically illustrates a top view of a second embodiment of eye drop dispenser holder 55, in accordance with some embodiments of the present invention.

Figure 10B:
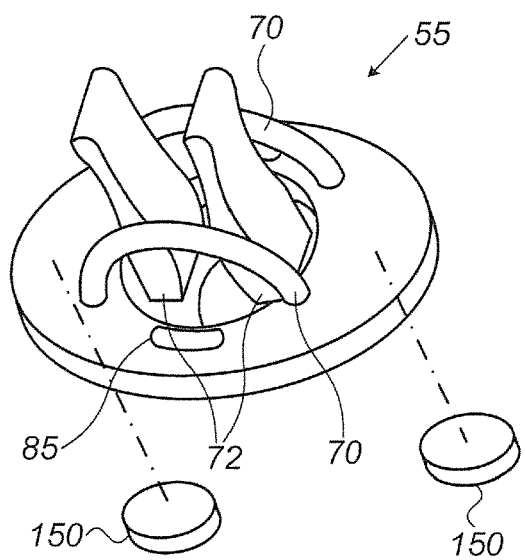
FIG. 10B schematically illustrates a top view of a second embodiment of an eye drop dispenser holder including magnets, in accordance with some embodiments of the present invention.

FIG. 10B schematically illustrates a top view of a second embodiment of eye drop dispenser holder 55 including magnets 150, in accordance with some embodiments of the present invention.

Figure 10C:
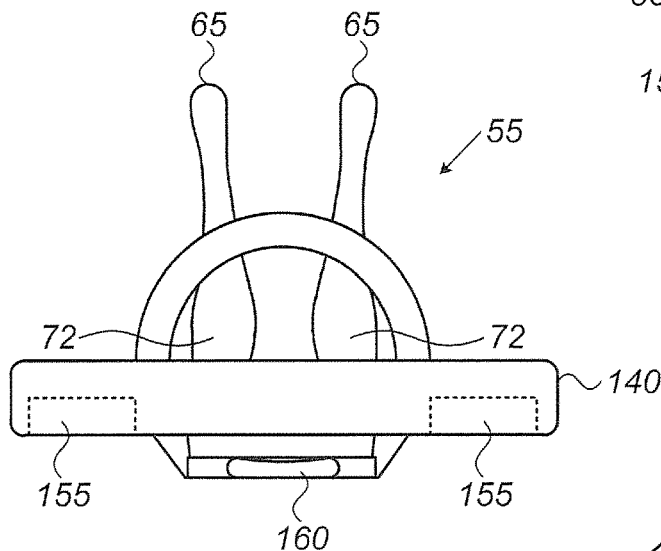
FIG. 10C schematically illustrates a side view of a second embodiment of an eye drop dispenser holder, in accordance with some embodiments of the present invention.

FIG. 10C schematically illustrates a side view of a second embodiment of eye drop dispenser holder 55, in accordance with some embodiments of the present invention.

Figure 10D:
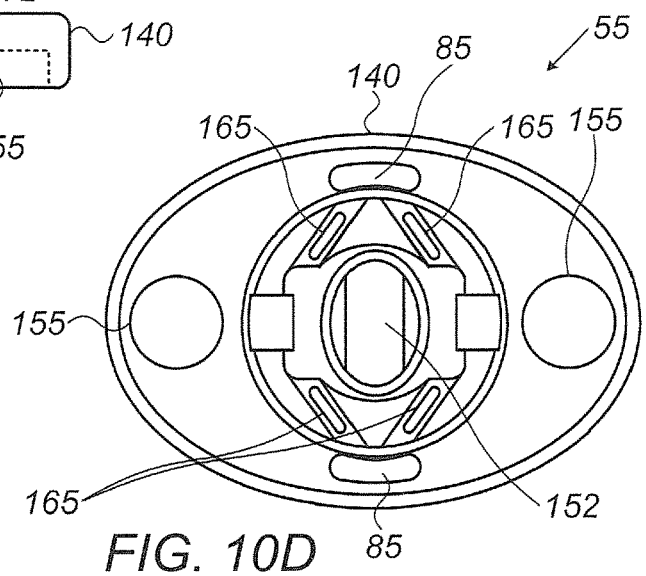
FIG. 10D schematically illustrates a bottom view of a second embodiment of an eye drop dispenser holder, in accordance with some embodiments of the present invention.

FIG. 10D schematically illustrates a bottom view of a second embodiment of eye drop dispenser holder 55, in accordance with some embodiments of the present invention. Magnets 150 may be installed in sockets 155. Fully assembled, eye drop dispenser holder 55 may be then removably attached to eye cup housing 15 to form eye drop guide device 50 as shown in FIGS. 4A-4B.

Figure 11:
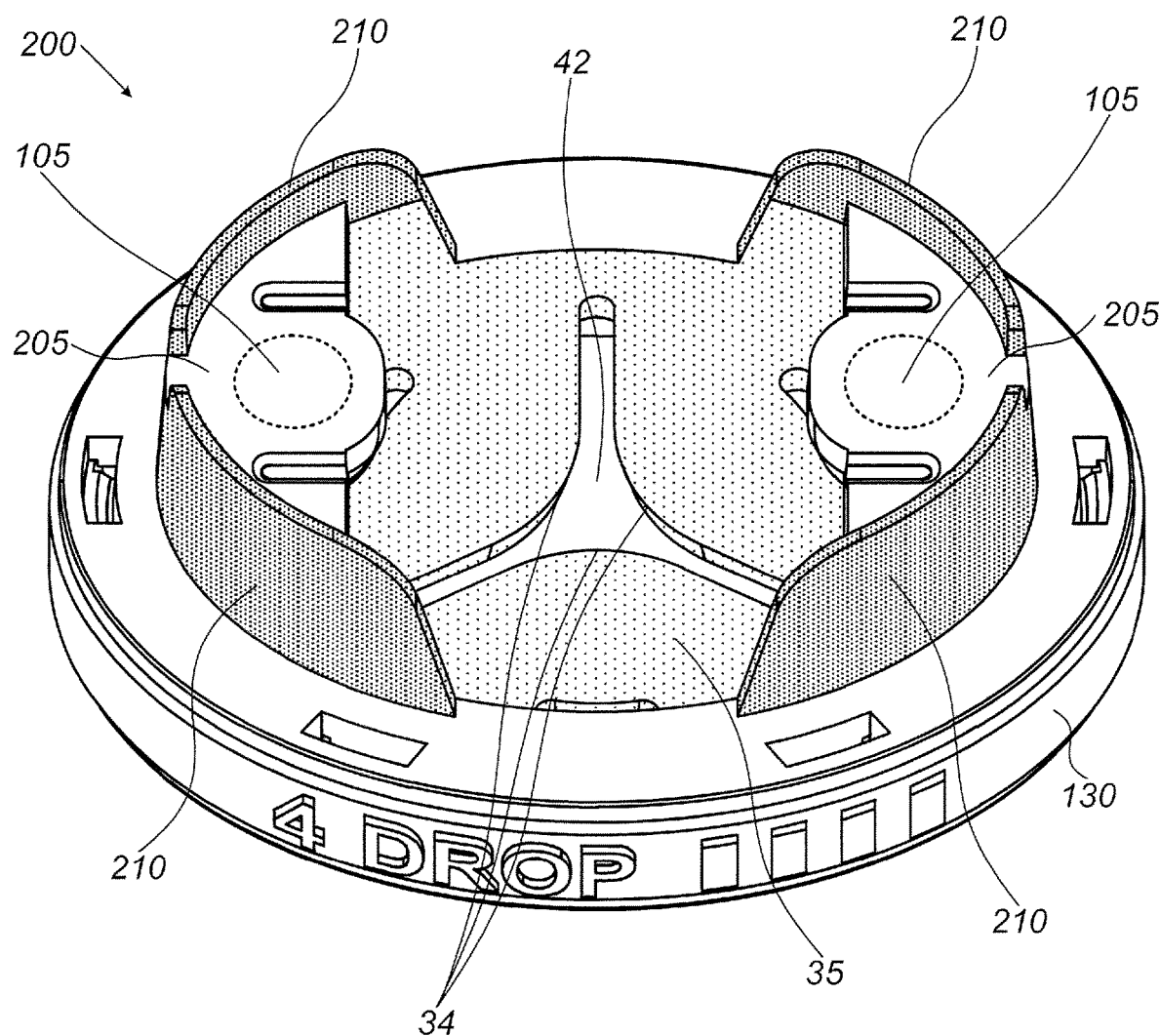
FIG. 11 schematically illustrates a top view of a third embodiment of an eye drop dispenser holder, in accordance with some embodiments of the present invention.

FIG. 11 schematically illustrates a top view of a third embodiment of an eye drop dispenser holder 200, in accordance with some embodiments of the present invention. Eye drop dispenser holder 200 may include the same elements as eye drop dispenser holder 30. However, a guide wall 210 may be formed in the body of eye drop dispenser holder 200. Guide walls 210 may be used to support second end 94 of eye cup housing 15 to eye drop dispenser holder 200 when eye cup housing 15 is magnetically snapped into eye drop dispenser holder 200. Guide walls 210 may be shaped to conform to the same shape, form factor, and contour of second end 94 of eye cup housing 15 as shown in FIG. 7A. Eye drop dispenser holder 200 may include tabs 205 for holding magnets 105 with a different form factor than tabs 38, in order to provide support for holding a portion of guide walls 210. In some other embodiments steel plates, or other material that magnets attract may replace magnets 105 held by tabs 105. Magnets 105 may be attached to tab 205 or placed securely within recesses (not shown) within tab 205. Thus, in assembling eye drop guide device 10, guide walls 210 improve the alignment, stability and auto-aiming of eye drops from tip 40 into eye 16 as eye cup housing 15 is more accurately attached to eye drop dispenser holder 200. In some other embodiments, as shown in FIG. 11 aperture 43 is formed by flaps 34 extending further into the center of aperture 42 forming a narrow elongated slit through which eye drops bottle can be fixed securely. According to this embodiment the narrow aperture 43 formed by flaps 34 provides additional flexibility which allows for the accommodation of various types of eye drop bottles. In accordance with this embodiment, prescription band 130 includes a visual and tactile indicia to assist user 12 to identifying the dosage (e.g., four eye drops to be instilled). In this embodiment, the tactile indicia is comprised of four raised shapes, such as dots or rectangular shapes that can be felt with the fingertips of the user.

In some embodiments of the present invention, eye drop dispenser holder 55 may be used to instill eye drops from minim 60. Minim 60 may be placed through a minim hole 152. The symmetry of eye drop dispenser holder 55 may ensure self-centering of tip 63 in the design of eye drop guide device 50 when minim 60 is placed in minim hole 152. This helps to ensure that when user 12 squeezes eye drops from minim 60, the eye drops will land (auto-aimed) substantially in the center of eye 16 (e.g., on cornea 14). Minim hole 152 may be large enough so as to accommodate different types of eye drop minim medications in eye drop dispenser holder 55.

In some embodiments of the present invention, eye drop dispenser holder 55 may be formed from nylon, which is strong, light-weight and flexible. Eye drop dispenser holder 55 may include light holes 85, finger squeeze tabs 65, minim pressure tabs 72, restrictors 70, sockets 155 for magnets 150, a minim landing pad 160, and compression truss 165.

In some embodiments of the present invention, light holes 85 may be used to provide a focal point for user 12 to look at when eye cup 25 is placed over eye 16 so as to reduce the tendency for user 12 to blink. Finger squeeze tabs 65 may be used by user 12 to squeeze eye drops from minim 60 to allow maximum pressure on minim 60 with minimal force by user 12. Finger squeeze tabs 65 may include an indentation in the form factor for finger placement. Minim pressure tabs 72 may include an area with extra thickness relative to finger squeeze tabs 65 which is the point of maximal pressure on minim 60.

In some embodiments of the present invention, restrictors 70 may be used as a safety feature to prevent minims 60 with irregular shapes, such as triangular-shaped minims, from moving or shaking inside eye drop dispenser holder 55. Restrictors 70 may include an arch-like structure on both sides of eye drop dispenser holder 55 so as to limit irregular shaped minims from travelling too close to eye 16. Minim landing pad 160 may be used as a safety feature to prevent contact between minim tip 63 and eye 16 by limiting the distance from minim tip 63 to eye 16 of user 12. Minim landing pad 160 may include a small platform to restrict minim 60 from over-displacement such that tip 63 may contact and possibly injure eye 16. Compression trusses 165 (e.g. four compression trusses 165 in FIG. 10D) may be used to evenly distribute the compression forces over the body of minim 60 induced by user 12 squeezing on finger squeeze tabs 65 and may provide for easier compression (e.g., easier squeezing by the user) on minim 60.

In some embodiments of the present invention, eye drop guide device 10 and/or 50 for instilling eye drops to eye 16 may include eye cup housing 15 and an eye drop dispenser holder 30 and/or 55. Eye cup housing 15 may include eye cup 25 at first end 92 of eye cup housing 15 configured to be placed over an eye, hole 87 through eye cup housing 15 at second end 94 of eye cup housing 15, and magnet 100 fixed to eye cup housing 15 at second end 94. Eye drop dispenser holder 30 and/or 55 may include magnet 105 and/or 150 fixed to eye drop dispenser holder 30. Magnet 100 in eye cup housing 15 and magnet 105 and/or 150 in eye drop dispenser holder 30 and/or 55 are configured to be attracted to one another so as to removably attach eye cup housing 15 to eye drop dispenser holder 30 and/or 55 that positions tip 40 and/or 63 of an eye drop dispenser 36 and/or 60 held by eye drop dispenser holder 30 and/or 55 to pass through hole 87 in eye cup housing 15 and into eye cup 25 for instilling eye drops into eye 16 (see FIG. 1C for eye drop device 10).

Eye drop guide device 10 and/or 50 may both use the same eye cup housing 15 which may be removably attached to eye drop dispenser holder 30 for eye drop bottle 36 and/or eye drop dispenser holder 55 for minims 60. Thus, patients that may require different types of medications in different eye drop in different eye drop dispenser packages such as eye drop bottles and/or minims may now interchangeably use both types of medication packages (e.g., eye drop bottle and/or minim) in the same eye drop guide by snapping in the two different eye drop dispenser holders to the eye cup housing.

In some embodiments of the present invention, the two eye drop guide devices taught herein may include two pairs of magnets. Eye cup housing 15 may include two magnets 100. Eye drop dispenser holder 30 may include two magnets 105 and eye drop dispenser holder 55 may include two magnets 150. In some embodiments, magnets 100, magnets 105, and magnets 150 may be the same type and size of magnet. In this case, when placing the magnets in the sockets 90 in eye cup housing 15 and in sockets 113 and sockets 155 in eye drop dispenser holder 30 and eye drop dispenser holder 50, respectively, magnets 100 should have an opposite polarity, for example, to that of magnets 105 and magnets 150. Otherwise, eye cup housing 20 may be magnetically repelled from eye drop dispenser holder 30 and eye drop dispenser holder 55 instead of being removably attached.

The embodiments herein are not limited to magnets in both sides of the eye guide devices 10 and 50 (e.g., eye cup housing 15 pairing with eye drop dispenser holder 30 and/or eye drop dispenser holder 55). Eye cup housing 15 may include magnets whereas eye drop dispenser holder 30 and/or eye drop dispenser holder 55 may include a metal in the respective sockets, for example, attached to the magnets in eye cup housing 15, or vice versa as described previously.

In some embodiments of the present invention, two magnets oriented in the sockets 113 in tabs 38 which are substantially opposite to one another in eye drop dispenser holder 30 and pairing to two magnets in eye cup housing 15 in sockets 90, which are substantially opposite to sockets 113, assist in self-centering eye cup housing 15 with eye drop dispenser holder 30 as the two pieces snap together.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. An eye drop guide for instilling eye drops to an eye, the eye drop guide comprising:
    an eye cup housing, comprising an eye cup at a first end of the eye cup housing configured to be placed over an eye, a hole through the eye cup housing at a second end of the eye cup housing, and a magnet fixed to the eye cup housing at the second end; and
    an eye drop dispenser holder, comprising a magnet fixed to the eye drop dispenser holder;
    wherein the magnet in the eye cup housing and the magnet in the eye drop dispenser holder are configured to be attracted to one another so as to removably attach the eye cup housing to the eye drop dispenser holder that positions a tip of an eye drop dispenser held by the eye drop dispenser holder to pass through the hole in the eye cup housing and into the eye cup for instilling eye drops into the eye,
    wherein the eye cup housing comprises an eye cup housing base, and an eye cup housing case with a socket at the second end formed therein adjacent to the hole and configured to be placed over the eye cup housing base and
    wherein the eye cup housing case affixes the magnet in the socket at the second end when placed over the eye cup housing base.

2. The eye drop guide of claim 1 wherein the eye drop dispenser holder, comprises a steel plate fixed to the eye drop dispenser holder;
    wherein the magnet in the eye cup housing and the steel plate in the eye drop dispenser holder are configured to be attracted to one another so as to removably attach the eye cup housing to the eye drop dispenser holder that positions a tip of an eye drop dispenser held by the eye drop dispenser holder to pass through the hole in the eye cup housing and into the eye cup for instilling eye drops into the eye.

3. The eye drop guide of claim 1, wherein the eye cup is contoured with a curvature of an eye socket.

4. The eye drop guide of claim 1, wherein the magnet is fixed to the eye cup housing by placing the magnet in a respective socket formed in the eye cup housing, and wherein the magnet is fixed to the eye drop dispenser holder by placing the magnet in a respective socket formed in the eye drop dispenser holder.

5. The eye drop guide of claim 1, wherein the eye cup housing comprises one or more light holes.

6. The eye drop guide of claim 1, wherein the eye cup and the eye cup housing base are formed from silicone.

7. The eye drop guide of claim 1, wherein the eye cup housing case is formed from a thermoplastic.

8. The eye drop guide of claim 1, wherein the eye drop dispenser holder comprises a guide wall configured to support the second end of the eye cup housing when attached to the eye drop dispenser holder.

9. The eye drop guide of claim 1, wherein a socket is formed in a tab attached to the eye drop dispenser holder for holding the magnet in the eye drop dispenser holder.

10. The eye drop guide of claim 1, wherein the eye drop dispenser holder comprises an eye drop dispenser holder body and an eye drop dispenser holder case.

11. The eye drop guide of claim 9, wherein the eye drop dispenser holder body and the eye drop dispenser holder case are formed from a thermoplastic.

12. The eye drop guide of claim 1, wherein the eye drop dispenser holder is configured to hold an eye drop bottle using a flexible membrane attached to the eye drop dispenser holder.

13. The eye drop guide of claim 11, wherein the flexible membrane comprises an aperture with flaps configured to hold a neck of the eye drop bottle.

14. The eye drop guide of claim 1, wherein the eye drop dispenser holder is configured to hold a minim in a minim hole formed in the eye drop dispenser holder.

15. The eye drop guide of claim 13, wherein the eye drop dispenser holder includes a landing pad.

16. The eye drop guide of claim 13, wherein the eye drop dispenser holder includes restrictors.

17. The eye drop guide of claim 13, wherein the eye drop dispenser holder includes finger squeeze tabs.

18. The eye drop guide of claim 13, wherein the eye drop dispenser holder includes compression trusses.

19. The eye drop guide of claim 13, wherein the eye drop dispenser holder is formed from nylon.

\* \* \* \* \*